United States Patent
Narbeshuber et al.

(10) Patent No.: US 6,262,325 B1
(45) Date of Patent: Jul. 17, 2001

(54) BASIC CATALYST BASED ON TITANATES, ZIRCONATES AND HAFNATES

(75) Inventors: Thomas Narbeshuber, Ibbenbüren; Ulrich Steinbrenner, Ludwigshafen, both of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/412,604

(22) Filed: Oct. 6, 1999

(30) Foreign Application Priority Data

Sep. 29, 1998 (DE) .............................. 198 44 705
Oct. 9, 1998 (DE) .............................. 198 46 549

(51) Int. Cl.$^7$ .............................. C07C 2/66; B01J 23/04; B01J 21/00
(52) U.S. Cl. .............................. 585/467; 585/446; 585/455; 502/344; 502/349; 502/525
(58) Field of Search .............................. 502/344, 349, 502/525; 585/446, 455, 467, 670, 510, 520, 530

(56) References Cited

U.S. PATENT DOCUMENTS

| | | | |
|---|---|---|---|
| 4,126,580 | * 11/1978 | Lauder .............................. | 502/525 |
| 4,134,852 | * 1/1979 | Volin .............................. | 502/344 |
| 4,151,123 | * 4/1979 | McCann, III .............................. | 502/525 |
| 4,522,706 | * 6/1985 | Wheelock et al. .............................. | 208/121 |
| 4,636,378 | * 1/1987 | Pastor et al. .............................. | 423/598 |
| 4,914,250 | 4/1990 | Smith .............................. | 585/452 |
| 4,922,054 | 5/1990 | Smith .............................. | 585/452 |
| 5,015,461 | * 5/1991 | Jacobson et al. .............................. | 423/593 |
| 5,097,088 | 3/1992 | Fukao et al. .............................. | 585/453 |
| 5,334,794 | 8/1994 | Fushimi et al. .............................. | 585/452 |

FOREIGN PATENT DOCUMENTS 636 597 A1  2/1995  (EP) .
51 63171    6/1993  (JP) .

* cited by examiner

*Primary Examiner*—Walter D. Griffin
(74) *Attorney, Agent, or Firm*—Keil & Weinkauf

(57) ABSTRACT

The catalyst comprises at least one alkali metal on a support which has the general formula (I)

$$A_n \cdot Ti_m \cdot Zr_p \cdot Hf_q \cdot O_{n'+2(m'+p'+q')} \quad (I)$$

where
A is a divalent metal,
$20 \cdot (m'+p'+q') > n' > 0.05 \cdot (m'+p'+q')$,
and which may be doped with at least one compound of an alkali metal and/or alkaline earth metal,
where the alkali metal/support ratio by weight is 0.01–5:1 and, when a dopant is present, the dopant/support ratio by weight is 0.01–5:1, and where the proportion of support phase corresponding to the $ZrO_2$ structure or an alkaline earth metal oxide structure or consisting of $ZrO_2$ or alkaline earth metal oxide is less than 10% by weight. The catalyst is used for the side-chain alkylation or alkenylation of alkylaromatic compounds with olefins or diolefins, for the double-bond isomerization of olefins, for the dimerization of olefins, for the coupling of aromatic nuclei and for the amination of olefins and conjugated diolefins.

11 Claims, No Drawings

BASIC CATALYST BASED ON TITANATES, ZIRCONATES AND HAFNATES

The invention relates to a catalyst, to the use thereof in reactions catalyzed by strong bases, and to a process for the side-chain alkylation or alkenylation of alkylaromatic or alkylalicyclic compounds with olefins or diolefins.

The side-chain alkylation, in particular of aromatic compounds having an acidic proton in the α position of the side chain, in the presence of catalysts is known.

EP-B-0 439 679 describes a process for the alkylation of alkylaromatic hydrocarbons. The reaction takes place in the presence of a catalyst composed of activated alumina doped with magnesium hydroxide and potassium metal. Also employed in place of magnesium hydroxide are calcium hydroxide, barium hydroxide or magnesium oxide. Impregnation with potassium hydride is also described.

U.S. Pat. No. 4,914,250 relates to a process for the side-chain alkylation of aromatic compounds. The catalyst employed in this case was diatomaceous earth which was present in the reaction mixture in addition to potassium or NaK and traces of water.

U.S. Pat. No. 4,922,054 likewise relates to a process for the side-chain alkylation of aromatic compounds in which diatomaceous earth was likewise employed as catalyst and was present in the reaction mixture in addition to NaK and potassium oxide. Rubidium oxide was also used in place of potassium oxide. Potassium metal was also employed in place of NaK.

JP-A-05 163 171 relates to the preparation of alkenylbenzene and its derivatives. The catalyst used comprises an alkali metal and a potassium carbonate salt and/or KOH, which are dispersed in the presence of an olefin and/or diolefin. Sodium metal is preferably used as alkali metal, and $K_2CO_3$, $KHCO_3$ or $KNaCO_3$ is preferably used as potassium carbonate salt.

The catalyst employed in EP-B-0 575 724 is prepared by impregnating zirconium oxide powder or potassium zirconate with potassium hydroxide solution, then calcining in air at 500° C. and applying metallic sodium to the support. The catalyst is employed for the side-chain alkenylation of o-xylene with butadiene.

EP-A-0 636 597 describes a process for the side-chain alkenylation of o-xylene with butadiene using as catalyst alumina, calcium oxide or zirconium oxide, each of which is impregnated with aqueous KOH and was then calcined at a temperature of from 500 to 550° C. The support is coated with metallic sodium.

These catalysts disclosed to date perform inadequately for many applications. On the one hand, the catalysts disclosed to date have low activity, which means that the space-time yield is very low. In addition there is formation of unwanted secondary products from the initially obtained primary products when the conversions are high and the service lives are prolonged. For example, in the side-chain alkylation of toluene with propene the formation of isobutylbenzene is followed by cyclizations to methylindan as well as dimerization of the olefin, for example formation of methylpentene from propene. In addition, the service life of the described catalysts is limited. As the reaction time increases, the catalysts lose activity and their byproduct spectrum shows some changes.

It is an object of the present invention to provide a catalyst for side-chain alkylation or alkenylation which avoids the disadvantages of the known catalysts and has a high activity, selectivity and service life.

We have found that this object is achieved by providing a catalyst comprising at least one alkali metal on a support which has the general formula (I)

$$A_{n'}Ti_{m'}Zr_{p'}Hf_{q'}O_{n'+2(m'+p'+q')} \qquad (I)$$

where

A is a divalent metal, $20 \cdot (m'+p'+q') > n' > 0.05 \cdot (m'+p'+q')$, and which may be doped with at least one compound of an alkali metal and/or alkaline earth metal, where the alkali metal/support ratio by weight is 0.01–5:1 and, when a dopant is present, the dopant/support ratio by weight is 0.01–5:1, and where the proportion of support phase corresponding to a $ZrO_2$ structure or an alkaline earth metal oxide structure or consisting of $ZrO_2$ or alkaline earth metal oxide is less than 10% by weight.

This object is further achieved by using this catalyst in reactions catalyzed by strong bases, preferably for the side-chain alkylation or side-chain alkenylation of alkylaromatic or alkylalicyclic compounds with olefins or diolefins, for the double-bond isomerization of olefins or for the dimerization of olefins.

The object is further achieved by way of example by providing a process for the side-chain alkylation or side-chain alkenylation of alkylaromatic compounds by reaction with olefins or diolefins, the reaction being carried out in the presence of a catalyst as described above.

The alkali metal/support ratio is in this connection preferably 0.01–2:1, particularly preferably 0.01–1:1. The alkali metal is moreover preferably sodium or potassium, in particular sodium. It is also possible to employ mixtures of several alkali metals.

The support consists in the undoped state of complex oxides of divalent metals A and tetravalent titanium, zirconium and/or hafnium. Examples of such oxides are titanates of the general formula $ATi_mO_{1+2m}$ such as $ATiO_3$, $ATi_2O_5$, $ATi_3O_7$, $ATi_4O_9$, $ATi_5O_{11}$ or $ATi_6O_{13}$, or of the general formula $A_{1+m}Ti_mO_{1+3m}$ (i.e. n=1+m) such as $A_2TiO_4$ or $A_3Ti_2O_7$, but also compounds which belong to neither of the homologous series defined by the above general formulae, such as $A_6Ti_{17}O_{40}$. Further oxides are also the compounds of tetravalent zirconium or hafnium corresponding to the titanates (zirconates and hafnates respectively), and the corresponding compounds of two metals, preferably of zirconium and hafnium or of titanium and zirconium, or of all three of said tetravalent metals (in which case the general formulae then correspond to those above), such as $ATi_2ZrO_7$, $ATiZr_2O_7$, $AZr_2HfO_7$ or $A_3ZrHfO_7$. A is preferably selected from Mg, Ca, Sr, Ba, Mn, Fe, Co, Ni, Pb, Zn, Cd, Pb and mixtures thereof, particularly preferably from Mg, Ca, Sr, Ba and mixtures thereof.

Typical representatives of the titanates are $ATiO_3$ with A=Mg, Ca, Sr, Ba, Fe, Cd and Zn, such as $MgTiO_3$ and $CaTiO_3$, $ATi_2O_5$ with A=Mg, Ca, Sr, Ba, Co and Fe, such as $MgTi_2O_5$, also $ATi_3O_7$, $ATi_4O_9$, $ATi_5O_{11}$, $ATi_6O_{13}$, $A_2TiO_4$ and $A_3Ti_2O_7$, with A=Mg, Ca, Sr and Ba, such as $CaTi_3O_7$, $BaTi_4O_9$, $Sr_3Ti_2O_7$ and $Ba_4Ti_{13}O_{30}$.

Typical representatives of the zirconates are $AZrO_3$ with A=Mg, Ca, Sr and Ba and Pb such as $CaZrO_3$ and $BaZrO_3$, $AZr_4O_9$ and $A_3Zr_2O_7$ with A=Mg, Ca, Sr and Ba such as $BaZr_4O_9$ and $Sr_3Zr_2O_7$.

Typical representatives of hafnates are $AHfO_3$ with A=Mg, Ca, Sr, Ba and Pb, and $AHf_4O_9$ and $A_3Hf_2O_7$ with A=Mg, Ca, Sr and Ba.

Typical representatives of compounds of titanium and zirconium or of zirconium and hafnium are, for example, $CaTiZr_2O_7$ and $CaTi_2ZrO_7$ or $CaZrHf_2O_7$ and $CaZr_2HfO_7$.

The term "support which has the general formula (I)" means that the support consists either of one of the compounds described above alone or of a defined mixture thereof, i.e. although in the individual compound types or in the individual compound the indices n, m, p, q and, when Zr and Hf are present, p+q (where m+p+q must never be 0) are integers, when the support is viewed as a whole, the indices n', m', p' and q' in the formula (I), which characterizes the support as a whole are values averaged over all individual values for individual compound types, i.e. apart from exceptions are not integers. In the limiting case of the presence of a single compound, n, m, p and q are identical to n', m', p' and q' and are thus integers.

The catalyst preferably contains the oxides of the general formulae $ATi_mO_{1+2m}$, $A_nTi_mO_{n+2m}$, $AZr_pO_{1+2p}$, $A_nZr_pO_{n+2p}$, $ATi_mZr_pO_{1+2(m+p)}$, $A_nTi_mZr_pO_{n+2(m+p)}$, with n, m, p and q being integers.

The support may moreover be doped with at least one compound of an alkali metal and/or alkaline earth metal in the dopant/support ratio by weight of 0.01–5:1, preferably 0.01–2:1 and in particular 0.01–1:1. The catalyst is preferably doped in this way. The supports are moreover doped in particular with soluble compounds of the alkali metals and/or alkaline earth metals, such as the oxides, hydroxides, carbonates, formates, acetates and/or oxalates. The hydroxides or carbonates are preferably employed, particularly preferably $K_2CO_3$ and/or KOH.

The proportion of the supports with a crystallographic phase corresponding to a $ZrO_2$ structure or an alkaline earth metal oxide structure or consisting of $ZrO_2$ or alkaline earth metal oxide in the supports according to the invention is <10% by weight, the meaning of the structures mentioned being that in the general formula (I) the sizes of the indices n', m', q' are negligible in comparison with p' for a $ZrO_2$ structure and those of m', p', q' are negligible in comparison with n' for an alkaline earth metal oxide structure.

Preparation of the Catalysts

The catalysts are prepared by applying at least one alkali metal to the support of the general formula (I) in the form of the molten alkali metal, or impregnating the support with solutions of an alkali metal azide, drying the support treated in this way and decomposing the alkali metal azide or vapor deposition of the alkali metal on the support, or impregnating the support with ammoniacal solutions of the alkali metal and removing the ammonia from the support treated in this way with the support of the general formula (I) having been, where appropriate, previously doped by impregnation with a solution of at least one compound of an alkali metal and/or alkaline earth metal, drying and calcining the doped support.

The doping which is to be carried out where appropriate takes place in a manner known per se by impregnating and subsequently calcining at temperatures in the range from 100 to 1500° C., preferably 250 to 1000° C., particularly preferably 250 to 350° C. This impregnation can be carried out with a solution of the compound of the alkali metal and/or alkaline earth metal in any suitable solvent. Aqueous solutions are preferably employed, in which case the water is removed after impregnation by drying the impregnated support. Calcination is also possible without previous drying, in which case the solvent escapes at the start of the calcination. The calcination of the doped support can be carried out under reduced pressure, under atmospheric pressure or under elevated pressure. It can moreover take place either in an oxygen-containing atmosphere or in an inert gas atmosphere, such as under helium, nitrogen or argon, or under a reactive gas atmosphere, such as under hydrogen, ammonia, carbon dioxide or carbon monoxide.

The alkali metals are applied to the, preferably doped, support in a manner known per se. This includes, for example, application in the molten state to the support at a temperature in the range from 100 to 300° C., as described in GB-A-1 143 993. For this purpose, the appropriate amount of the alkali metal is added as ribbon or blocks to the support and mixed with it while heating. During this, the alkali metal is finely distributed on the support.

It is also possible to apply the alkali metals by impregnating with solutions of the alkali metal azides and then thermally decomposing the azides. A corresponding process is described, for example, in FR-A-2 609 024. The alkali metals can also be applied to the support by vapor deposition. This usually takes place under reduced pressure.

The supports can also be impregnated with ammoniacal solutions of the alkali metals, and the ammonia can then be evaporated.

The application of the alkali metals takes place in vacuo, under an inert gas atmosphere (He, $N_2$, Ar etc.) or under a reactive gas atmosphere ($H_2$, $CO_2$, CO).

The catalysts are employed in reactions catalyzed by strong bases, preferably for the side-chain alkylation or alkenylation of alkylaromatic compounds with olefins or diolefins, for the double-bond isomerization of olefins, for the dimerization of olefins, the coupling of aromatic nuclei and for the amination of olefins and conjugated diolefins.

The reaction in these cases is generally carried out at a temperature from −50 to 400° C., preferably from −20 to 300° C., particularly preferably from 80 to 250° C., and especially from 100 to 220° C. under a pressure of, preferably, from 0.1 to 200, particularly preferably from 1 to 150, especially from 1 to 100, bar.

All suitable alkylaromatic compounds can be employed. They may have as aromatic nucleus for example a benzene or naphthalene nucleus. Also suitable are alkylalicyclic compounds in which the cyclic nucleus can be a cyclic alkyl, alkenyl or alkynyl radical. It is also possible to employ radicals in which a plurality of ring structures are linked together. The ring structures have an acidic hydrogen atom in the α position of the side chain. They preferably have at least one alkyl radical bonded to the cyclic structure. The alkyl radicals may moreover have any length and be substituted by further substituents. The alkylaromatic compounds preferably employed are benzenes substituted by 1 to 6, preferably 1 to 3, in particular 1 to 2, $C_{1-20}$-alkyl radicals, preferably $C_{1-3}$-alkyl radicals, or naphthalenes substituted by 1 to 10, preferably 1 to 5, particularly preferably 1 to 2, $C_{1-20}$-, preferably $C_{1-3}$-alkyl radicals.

The olefins preferably have 2 to 20, particularly preferably 2 to 10, especially 2 to 5, C atoms. Those preferably employed are ethene, propene, 1-butene, 2-butene, isobutene, 1-pentene, 2-pentene, 2-methyl-1-butene, 2-methyl-2-butene and/or 3-methyl-1-butene. Ethene and propene are particularly preferred. The diolefins preferably have 4 to 20, particularly preferably 4 to 10, especially 4 to 6, C atoms. Butadiene and/or isoprene are particularly preferably employed. Particular preference is given to the reaction of toluene with ethene or propene to give propylbenzene or isobutylbenzene, the reaction of cumene with ethene to give tert-amylbenzene and the reaction of xylenes with butadiene to give 5-tolylpentenes.

Preferred reactions for coupling aromatic nuclei start from benzene, toluene, ethylbenzene, pyridine and naphthalene. Preferred aminations are the amination of ethene and isoprene.

The reaction can be carried out batchwise or, preferably, continuously in the liquid or gas phase, preferably in the liquid phase. The known apparatuses can moreover be employed for carrying out the process.

The invention is illustrated further by means of Examples below.

EXAMPLES

Preparation Examples

Catalyst A (Comparative)

γ-$Al_2O_3$ was impregnated with 10% by weight of $K_2CO_3$ (dissolved in $H_2O$). The suspension was evaporated to dryness, and the powder obtained in this way was calcined in a stream of air at 500° C. The material was then dried by stirring at 300° C. in vacuo for 3 h. 10% by weight metallic sodium was added to this powder and dispersed at 300° C.

Catalyst B (Comparative)

Precipitated $ZrO_2$.aq (equivalent to 37 g of $ZrO_2$) was impregnated with 3.7 g of wet KOH and dried at 300° C. for 16 h. 1 g of Na was added to 10 g of the powder obtained in this way and was dispersed at 300° C.

Catalyst C (Comparative)

30 g of $TiO_2$ (rutile, produced by BASF AG) were impregnated with 3 g of wet $K_2CO_3$ and calcined at 500° C. for 16 h. 1 g of Na was added to 10 g of the powder obtained in this way and was dispersed at 300° C.

Catalyst D

Precipitated $ZrO_2$.aq (equivalent to 6.16 g of $ZrO_2$) was impregnated with 33.3 ml of a 1.5 molar Ba(OAc)$_2$ solution, and the suspension was evaporated to dryness, dried at 150° C. and calcined at 800° C. for 33 h. 10 g of the $BaZrO_3$ (determined by X-ray diffractometry) obtained in this way were then treated with 1 g of $K_2CO_3$ in aqueous solution and dried at 350° C., and finally 1 g of metallic sodium was added to this powder and dispersed at 300° C.

Catalyst E 45.6 g of Ti(OEt)$_4$ was stirred into 100 ml of a two-molar Mg(OAc)$_2$ solution, and the resulting suspension was evaporated to dryness, dried at 150° C. and calcined at 800° C. for 33 h. 10 g of the $MgTiO_3$ (determined by X-ray diffractometry) obtained in this way were then treated with 1 g of $K_2CO_3$ in aqueous solution and dried at 400° C., and 1 g of metallic sodium was then added to this powder and dispersed at 300° C.

Catalyst F

Precipitated $ZrO_2$.aq (equivalent to 12.32 g of $ZrO_2$) was impregnated with 100 ml of a 1 molar Ca(OAc)$_2$ solution, and the suspension was evaporated to dryness, dried at 150° C. and calcined at 800° C. for 33 h. 10 g of the $CaZrO_3$ (determined by X-ray diffractometry) obtained in this way were then treated with 1 g of $K_2CO_3$ in aqueous solution and dried at 400° C., and 1 g of metallic sodium was then added to this powder and dispersed at 300° C.

Catalyst G 12.1 g of Ca were dissolved in 400 ml of EtOH, and then 68.37 g of Ti(OEt)$_4$ were added. The resulting ethanolate solution was vigorously stirred with a mixture of 30 g of $H_2O$ and 50 g of EtOH to form a gel, which was stirred for 1 h, dried in vacuo at 50° C. and calcined at 600° C. for 5 h. 10 g of the perovskite $CaTiO_3$ (determined by X-ray diffractometry) obtained in this way were then treated with 1 g of $K_2CO_3$ in aqueous solution and dried at 400° C., and then 1 g of metallic sodium was added to this powder and dispersed at 300° C.

Process Examples

Comparative Example C1–C3

10 g of catalyst A to C were introduced with 85 g of toluene into a pressure-tight reaction vessel. After addition of 20 g of propene, the reaction vessel was heated to 160° C. and the reaction suspension was then stirred for 12 h. The results are listed in Table 1.

Examples 1 to 4

10 g of catalysts D to G were introduced with 85 g of toluene into a pressure-tight reaction vessel. After addition of 20 g of propene, the reaction vessel was heated to 160° C. and the reaction suspension was then stirred for 12 h. The results are listed in Table 1.

TABLE 1

| | Cata-lyst | based on propene | | | based on toluene | |
|---|---|---|---|---|---|---|
| | | C | $S_{iBB}$ | $S_{Mepentene}$ | C | $S_{iBB}$ |
| Comparative Example C1 | A | 39 | 55 | 40 | 12 | 92 |
| Comparative Example C2 | B | 36 | 59 | 36 | 11 | 93 |
| Comparative Example C3 | C | 3 | 63 | 27 | 1 | 86 |
| Example 1 | D | 60 | 70 | 20 | 24 | 87 |
| Example 2 | E | 46 | 74 | 19 | 19 | 90 |
| Example 3 | F | 39 | 70 | 21 | 16 | 88 |
| Example 4 | G | 52 | 72 | 19 | 21 | 89 |

C = conversion [mol %]
$S_{iBB}$ = selectivity for isobutylbenzene [mol %]
$S_{Mepentene}$ = selectivity for methylpentene [mol %]

We claim:

1. A catalyst comprising at least one alkali metal on a support which has the general formula (I)

$$A_{n'}Ti_{m'}Zr_{p'}Hf_{q'}O_{n'+2(m'+p'+q')} \quad (I)$$

where

A is a divalent metal,

20·(m'+p'+q')>n'>0.05·(m'+p'+q'), and which may be doped with at least one compound of an alkali metal and/or alkaline earth metal, where the alkali metal/support ratio by weight is 0.01–5:1 and, when a dopant is present, the dopant/support ratio by weight is 0.01–5:1, and where the proportion of support phase corresponding to a $ZrO_2$ structure or an alkaline earth metal oxide structure or consisting of $ZrO_2$ or alkaline earth metal oxide is less than 10% by weight.

2. A catalyst as claimed in claim 1, wherein the support in the undoped state consists of complex oxides of divalent metals A and tetravalent titanium (Ti), zirconium (Zr) and/or hafnium (Hf).

3. A catalyst as claimed in claim 2, wherein the oxides of the general formulae $ATi_mO_{1+2m}$, $A_nTi_mO_{n+2m}$, $AZr_pO_{1+2p}$, $A_nZr_pO_{n+2p}$, $ATi_mZr_pO_{1+2(m+p)}$, $A_nTi_mZr_pO_{n+2(m+p)}$, with n, m, p and q being integers, are present.

4. A catalyst as claimed in claim 1, wherein A is selected from the group consisting of Mg, Ca, Sr, Ba, Mn, Fe, Co, Ni, Zn, Cd, Pb and mixtures thereof.

5. A catalyst as claimed in claim 1, with obligatory doping with at least one hydroxide or carbonate of an alkali metal and/or alkaline earth metal.

6. A process for preparing a catalyst as defined in claim 1 by applying at least one alkali metal to the support of the general formula (I) in the form of the molten alkali metal, or impregnating the support with solutions of an alkali metal azide, drying the support and decomposing the alkali metal azide or vapor deposition of the alkali metal on the support, or impregnating the support with ammoniacal solutions of the alkali metal and removing the ammonia with the support of the general formula (I) having been, where appropriate, previously doped by impregnation with a solution of at least one compound of an alkali metal and/or alkaline earth metal, drying and calcining the doped support.

7. A process for the side-chain alkylation or alkenylation of alkylaromatic compounds by, which comprises reacting olefins or diolefins with alkylaromatics in the presence of a catalyst as defined in claim 1.

8. A process as claimed in claim 7, wherein the reaction is carried out at a temperature in the range from −50 to 400° C. under a pressure in the range from 0.1 to 200 bar.

9. A process as claimed in claim 7, wherein benzenes substituted by 1 to 6 $C_{1-20}$-alkyl radicals and naphthalenes substituted by 1 to 10 $C_{1-20}$-alkyl radicals are employed as alkylaromatic compounds.

10. A process as claimed in claim 7, wherein ethene, propene, 1-butene, 2-butene, isobutene, 1-pentene, 2-pentene, 2-methyl-1-butene, 2-methyl-2-butene and/or 3-methyl-1-butene are employed as olefins, and butadiene or isoprene are employed as diolefins.

11. A process as claimed in claim 7, which is carried out continuously in the liquid or gas phase.

* * * * *